(12) United States Patent
Corcoran

(10) Patent No.: US 6,589,161 B2
(45) Date of Patent: Jul. 8, 2003

(54) CONSTRICTION DEVICE INCLUDING TEAR RESISTANT STRUCTURES

(75) Inventor: Dean T. Corcoran, Bothell, WA (US)

(73) Assignee: Spiration, Inc., Redmond, WA (US)

( * ) Notice: Subject to any disclaimer, the term of this patent is extended or adjusted under 35 U.S.C. 154(b) by 0 days.

(21) Appl. No.: 10/041,907

(22) Filed: Oct. 18, 2001

(65) Prior Publication Data

US 2003/0078469 A1 Apr. 24, 2003

(51) Int. Cl.[7] ................................................. A61F 2/00
(52) U.S. Cl. ........................................................ 600/37
(58) Field of Search ............................ 600/37; 602/62; 601/149, 152, 134; 607/2; 606/140; 2/403; 623/8; 181/251; 128/844

(56) References Cited

U.S. PATENT DOCUMENTS

| 4,685,534 A | * | 8/1987 | Burstein et al. ............. 181/251 |
| 4,738,249 A | * | 4/1988 | Linman et al. .............. 601/152 |
| 5,330,528 A | * | 7/1994 | Lazim ........................ 623/1.25 |
| 5,711,760 A | * | 1/1998 | Ibrahim et al. .............. 601/149 |
| 5,916,183 A | * | 6/1999 | Reid ........................... 601/134 |
| 6,059,797 A | * | 5/2000 | Mears ......................... 606/140 |
| 6,061,840 A | * | 5/2000 | Alligator ....................... 2/403 |
| 6,076,013 A | * | 6/2000 | Brennan et al. ............... 607/2 |
| 6,224,564 B1 | * | 5/2001 | Korobow ..................... 602/62 |
| 6,453,903 B1 | * | 9/2002 | Thomas, III ................. 128/844 |

* cited by examiner

Primary Examiner—Eric F. Winakur
Assistant Examiner—Nikita Veniaminov
(74) Attorney, Agent, or Firm—Graybeal Jackson Haley LLP

(57) ABSTRACT

A constriction device that constricts body tissue and is formed of relatively thin elastic material includes a tear resistance structure to preclude an inadvertent tear in the device from propagating through the device. The tear resistance structure includes a plurality of intersecting ribs formed in the elastic material. The ribs circumscribe the device and define rectangular, square, diamond, wavy, or knurled patterns.

23 Claims, 2 Drawing Sheets

CONSTRICTION DEVICE INCLUDING TEAR RESISTANT STRUCTURES

BACKGROUND OF THE INVENTION

The present invention is generally directed to a constriction device that constricts body tissue. The present invention is more particularly directed to a constriction device that includes tear resistant structures to preclude propagation of a tear in the device for protecting the integrity of the constriction device.

Constriction devices have been contemplated for constricting body tissue. Such devices have been considered for use, for example, in tissue resection procedures and in treating pulmonary disease.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and had increased 33% since 1979.

COPD affects the patient's whole life. It has three main symptoms: cough; breathlessness; and wheeze. At first, breathlessness may be noticed when running for a bus, digging in the garden, or walking up hill. Later, it may be noticed when simply walking in the kitchen. Over time, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled β-agonists. For those patients who respond poorly to the foregoing or who have persistent symptoms, Ipratropium bromide may be indicated. Further, courses of steroids, such as corticosteroids, may be required. Lastly, antibiotics may be required to prevent infections and influenza and pheumococcal vaccines may be routinely administered. Unfortunately, there is no evidence that early, regular use of pharmacotherapy will alter the progression of COPD.

Lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopped remitting for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life.

Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

The improvements in pulmonary function resulting from LVRS cannot be ignored. However, the surgery is very invasive and fraught with complications. Among the complications is the potential for lung air leaks. Lung tissue is very thin, and fragile hence difficult to suture together. After a lung portion is sectioned and removed, the remaining lung is most often restructured with suture staples. In about thirty percent (30%) of the cases, the difficulty with suturing lung tissue results in air leaks. Treatment for such air leaks depends upon their severity and often, in the most serious cases, requires further open chest surgery.

Air leaks in lungs can be caused by other causes. With increasing age, a patient may develop a weakened section of lung which may then rupture due to an extreme pressure differential, such as may result from simply a hard sneeze. AIDS patients can suffer from air leaks in their lungs. Air leaks in lungs can further be caused by a puncture from a broken rib or a stab wound.

The invention disclosed and claimed in copending U.S. application Ser. No. 09/534,244, incorporated herein by reference, provides an improved therapy for treating COPD and air leaks in lungs. The therapy includes a constriction device which, when deployed on a lung, suppresses air leaks in the lung tissue without requiring any suturing of the effected lung tissue. Still further, by constricting a large enough portion of a lung with the device, lung volume reduction with the concomitant improved pulmonary function may be obtained without the need for any suturing of lung tissue at all.

The lung constriction device includes a jacket or sheath of flexible material configured to cover at least a portion of a lung. The jacket has a pair of opened ends to permit the lung portion to be drawn into the jacket. The jacket is dimensioned to constrict the lung portion after the lung portion is drawn therein. The lung constriction device is preferably formed of expandable, such as elastic, material for receiving the lung tissue while the device is in an expanded or enlarged condition, and then contractible about the lung portion upon release of the expanded condition for constricting the lung tissue.

An important aspect of the device and method disclosed in U.S. application Ser. No. 09/534,244 is the ability to sever the constricting device intermediate its ends. This allows a significant portion of the constricted lung tissue to be removed altogether while permitting a portion of the constricting device to remain in the body for continued suppression of air leaks and maintenance of the remaining lung tissue integrity.

Devices and methods similar to those disclosed in U.S. application Ser. No. 09/534,244 may be employed to advantage in other and different procedures such as in general resection procedures and for body tissue other than lung tissue. Resection procedures are commonly performed for such body tissue as, for example, atrial appendage tissue, ovarian tissue, gall bladder tissue, pancreatic tissue, appendix tissue and spleen tissue. Resection procedures may be required to treat cancer, organ damage, or organ disease, for example.

U.S. application Ser. No. 09/534,244 also discloses and claims various methods and apparatus for deploying the constricting device on body tissue such as lung tissue. One apparatus and method contemplates mechanically expanding the device in a transverse dimension while physically pulling the tissue to be constricted into the device.

Another method contemplates mounting the device over a vacuum chamber and pulling the tissue into the vacuum chamber by engaging the tissue with an opened end of the chamber and then drawing a vacuum in the chamber. This draws the tissue into the chamber. Then, the chamber is withdrawn from the device, leaving the tissue constricted in the device.

A further method contemplates inserting the device into a vacuum chamber and sealing the opened end of the chamber to the device. The opened end of the chamber and the tissue are then brought into sealing engagement. A vacuum is next pulled in the chamber and the device to pull the tissue into the device and chamber. Once the tissue is within the device, the chamber is removed from over the device leaving the tissue constricted in the device.

Although various methods and apparatus have been conceived for effectively deploying constriction devices on body tissue, the constriction devices, over time, may become dislodged due to the nature of the soft tissue on which they are deployed. More specifically, soft body tissue has a tendency to expand at the proximal end of the device causing longitudinal slippage of the device on the body tissue. This may eventually lead to the device slipping totally free from the tissue.

To meet the needs for fixation, U.S. application Ser. No. 09/902,821, filed Jul. 10, 2001, and incorporated herein by reference, discloses and claims a constriction device having positive fixation structure for maintaining the constriction device deployed on the body tissue.

One disclosed device includes a plurality of fixation elements on the inner surface of the sleeve that grasp the body tissue upon release of the sleeve from the expanded condition. More particularly, the fixation elements are adjacent to one of the opposed openings and arranged in a side-by-side relation to grasp the body tissue between adjacent fixation elements when the sleeve is released from the expanded condition. The fixation elements may be integral to the longitudinal side wall or adhered to the inner surface of the sleeve. Still further, the inner surfaces of the fixation elements may have roughened surfaces to further assist in grasping the constricted body tissue.

While the fixation structures disclosed and claimed in the aforementioned U.S. application Ser. No. 09/902,821 are believed to be sufficient alone for maintaining the constriction device on the constricted body tissue, other forms of fixation may be further employed alone or in combination with the above described fixation structures for maintaining the constriction device on the constricted body tissue. One additional form of fixation widely practiced in the medical field is suturing.

While suturing would appear to be an option, simply suturing the constriction device to the constricted body tissue would pose a number of problems. Such problems would arise because the material from which the constriction device is formed is relatively thin elastic material. The suturing of such material could easily cause tearing of the device by the suture. Moreover, the very act of puncturing the device material with a suture needle could readily cause tearing of the device material. Copending U.S. application Ser. No. (9/969,949) filed Oct. 2, 2001 and incorporated herein by reference discloses a constriction device configured to permit the suturing of the device to constricted body tissue while protecting against tearing of the device material by either the suture or a suture needle.

In one disclosed embodiment, the device has an increased thickness about each suture hole to reinforce the suture holes. The increased thickness may have a tapered cross-section for guiding a suture needle into the suture holes and may extend from the inner surface of the device or from the outer surface of the device.

While the suture hole reinforcement mentioned above represents an important advancement towards protecting the constriction device against tears during suturing, there is still the possibility that the device may be accidentally punctured or torn outside of a suture hole during deployment. Since, as previously mentioned, the device takes the form of a sleeve formed of relatively thin elastic material, still further tear resistance would be helpful for protecting against tear propagation. The present invention provides such additional tear propagation protection.

SUMMARY OF THE INVENTION

The present invention provides a constriction device that is tear resistant. The device includes an elongated sleeve having at least one opened end and being formed from elastic material to receive, when in an expanded condition, body tissue to be constricted and to constrict the body tissue when released from the expanded condition. The device further includes a tear resistance structure about the sleeve that precludes propagation of a tear in the sleeve.

The tear resistance structure may be an increased thickness of the sleeve defining a plurality of ribs in the sleeve. The plurality of ribs may include a first plurality of ribs and a second plurality of ribs which intersect each other. The intersecting ribs may define a pattern of squares, a pattern of diamonds, a pattern including waves, or a knurled pattern. Preferably the ribs are formed on an inner surface of the sleeve.

The present invention further provides a constriction device that constricts body tissue, the device including sleeve means formed of elastic material including at least one opened end for constricting body tissue received therein and tear resistance means about the sleeve for precluding propagation of a tear in the sleeve means.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION

Figure 1:
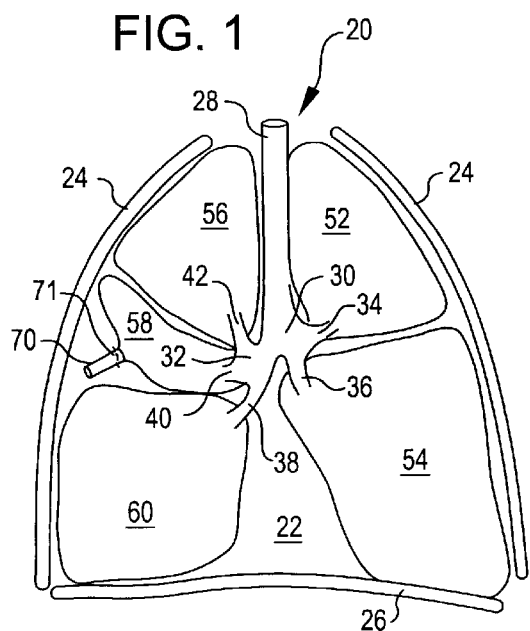
FIG. 1 is a simplified sectional view of a thorax illustrating a respiratory system having a constricting device embodying the present invention deployed on a portion of a lung to effect lung volume reduction.

Referring now to FIG. 1, it is a sectional view of a respiratory system 20. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, and the bronchial branches 34, 36, 38, 40, and 42. The respiratory system 20 further includes left lung lobes 52 and 54 and right lung lobes 56, 58, and 60. Each bronchial branch communicates with a respective different portion of a lung lobe, either the entire lung lobe or a portion thereof.

A healthy respiratory system has an arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air to an inflated condition. When the individual exhales, the diaphragm returns to its original arched condition to decrease the volume of the thorax. The decreased volume of the thorax causes a positive pressure within the thorax which in turn causes exhalation of the lung lobes.

FIG. 1 also shows a constriction device 70 embodying the present invention deployed on lobe 58. The device 70 is configured as a sleeve or sheath formed of a sheet of elastic biocompatible material. The material may be formed from silicone rubber, polyurethane, expanded polytetraflouroethylene, polyester and polyurethane, or nylon and polyurethane, for example. The sleeve is preferably opened at both ends and may be generally cylindrical in configuration.

The sleeve may be applied to the lung lobe while in an expanded condition. This may be accomplished by expanding the sleeve with a vacuum and then pulling the lung portion into the sleeve with the vacuum. When the lung portion is within the sleeve, the expansion of the device is released. With the expansion released, the sleeve is permitted to contract or collapse about the lung portion to constrict the lung portion.

The device 70 may be employed, for example, to suppress air leakages in lungs. It may also find use to advantage in constricting a lung portion suffering from COPD to simulate or achieve lung volume reduction. All of the beneficial effects of lung volume reduction surgery may be realized and, most importantly, without requiring suturing of lung tissue. The constriction device 70 is sutured to the constricted lung tissue by a suture 71. To that end, the device 70 preferably includes a plurality of suture holes reinforced in accordance with one of the embodiments described in the aforementioned pending U.S. application Ser. No. (9/969, 949) so that neither the suture needle nor the suture tears or adversely affects the integrity of the device 70.

Figure 2:
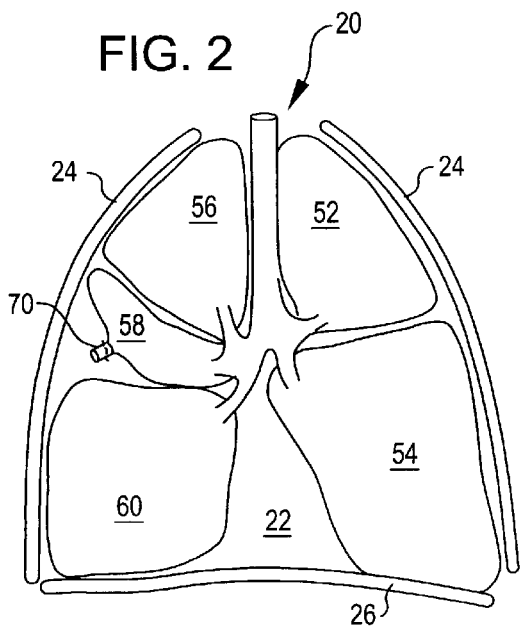
FIG. 2 is a sectional view similar to FIG. 1 but illustrating the respiratory system after the constricted lung portion has been resectioned.

FIG. 2 shows the respiratory system 20 after the constricted lung portion has been resectioned. The device 70 is preferably formed of severable material, such as, any of the materials previously described. This enables the device 70 to be severed or cut intermediate its ends with a suitable bladed instrument to resection the lung lobe 58. The portion of the device 70 remaining on the lobe 58 continues to constrict the lung tissue therein to form an effective seal from leakage. The suture 71 continues to maintain the device 70 on the remaining constricted tissue. Hence, lung volume reduction is rendered an available treatment while negating the need of conventional lung sectioning and avoiding the potentially severe complications which accompany such a procedure.

Figure 3:
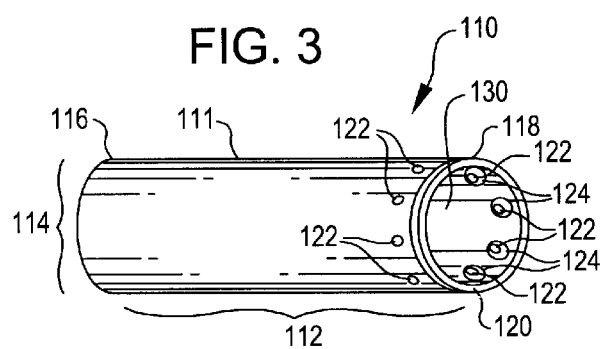
FIG. 3 is a perspective view illustrating a constricting device embodying the present invention.
Figure 4:
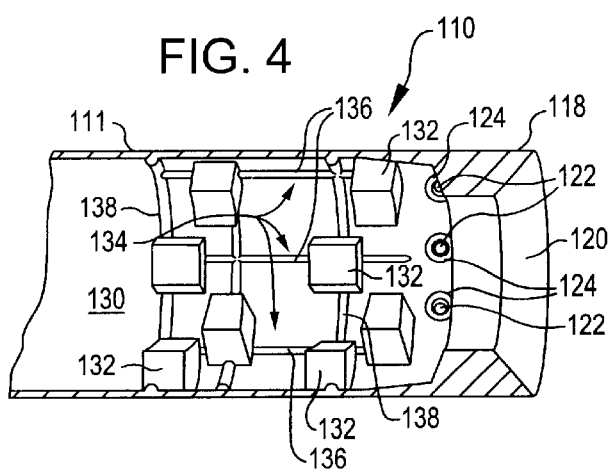
FIG. 4 is a perspective view of the interior of the device of FIG. 3 illustrating a tear resistance structure embodying the present invention.

FIGS. 3 and 4 illustrate a constriction device 110 embodying the present invention. As generally illustrated in FIG. 3, the device 110 is a generally cylindrical sleeve 111 having a longitudinal dimension 112 and a transverse dimension 114. As previously mentioned, the device 110 is preferably formed of a relatively thin elastic material permitting the device to expand in the longitudinal dimension and more importantly in the transverse dimension. For example, the device 110 may be formed from silicone. The device 110 has opposed opened ends 116 and 118. The device may further include at one end, for example, end 118, an integral rim 120.

The device 110 further includes a plurality of suture holes 122. The suture holes 122 are preferably distributed about the device closely adjacent the opened end 118. About each suture hole 122 is a suture hole reinforcement structure 124. The suture hole reinforcement structure 124 of each suture hole 122 is an increased thickness or thickened portion in the sleeve wall forming a ring shaped structure about each suture hole on the inner surface 130 of the sleeve 111. The reinforcement structure 124 of each suture hole 122 may further define a tapered surface to help guide a suture needle through its corresponding suture hole.

As may be best seen in FIG. 4, the device 110 further includes a plurality of fixation elements 132. The fixation elements are arranged in side-by-side relation and project inwardly from the inner surface 130 of the sleeve 111. As described in the aforementioned U.S. application Ser. No. 09/902,821, adjacent fixation elements 132 grasp the body tissue upon deployment of the sleeve to further maintain the device 110 on the constricted body tissue.

With continued reference to FIG. 4, and in accordance with the present invention, the device 110 includes a tear resistance structure 134. The tear resistance structure 134, in accordance with this embodiment, is an increased thickness in the sleeve 111 defining a plurality of ribs or ridges including a first plurality 136 of ribs and second plurality 138 of ribs. The ribs 136 and 138 are formed on the inner surface 130 of the sleeve 111. The ribs are further arranged so that the first plurality 136 and second plurality 138 of ribs intersect each other. Here, the ribs intersect to form a pattern of rectangles. The rib pattern circumscribes the sleeve 111. By virtue of the tear resistance structure of the rib pattern, any nick or tear will be precluded from propagating beyond the ribs or ridges enclosing the nick or tear. As a result, the overall integrity of the device 110 is protected notwithstanding an accidental or inadvertent nick or tear in the elastic material of the sleeve 111.

Figure 5:
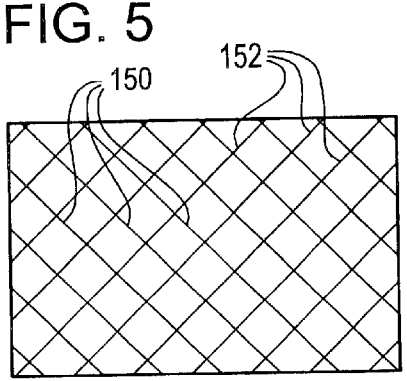
FIG. 5 is a plan view of one tear resistance structure pattern embodying the present invention.
Figure 6:
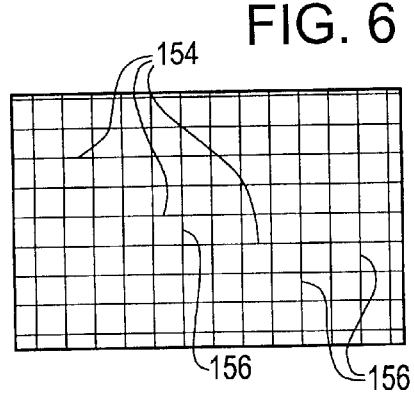
FIG. 6 is a plan view of another tear resistance structure pattern configured in accordance with another embodiment of the present invention.
Figure 7:
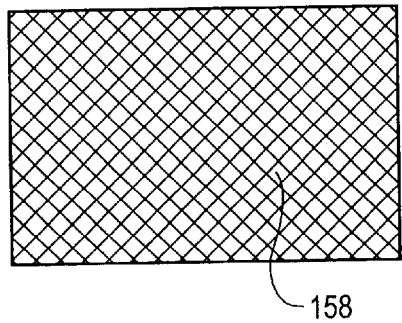
FIG. 7 is a further plan view of still another tear resistance structure pattern embodying the present invention.
Figure 8:
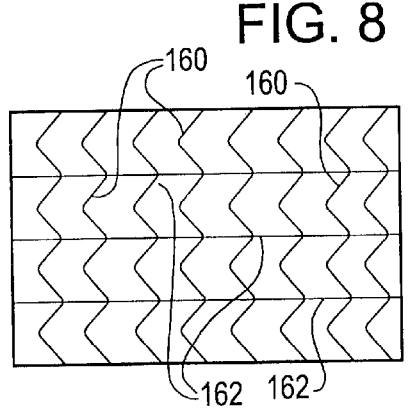
FIG. 8 is a still further plan view of another tear resistance structure pattern embodying the present invention.

FIG. 5 shows another pattern in which the tear resistance ribs may be formed. Here, first and second pluralities 150 and 152 of ribs intersect to form a diamond pattern. Other patterns are shown in FIGS. 6–8. In FIG. 6, first and second pluralities 154 and 156 of ribs intersect to form a pattern of squares. In FIG. 7, the ribs form a knurled pattern 158. In FIG. 8 a first plurality 160 of ribs form a pattern of waves which intersect a second plurality 162 of substantially parallel ribs. As will be appreciated by those skilled in the art, other rib patterns may be used without departing from the present invention.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A constriction device that constricts internal body tissue, the device comprising:
    an implantable elongated sleeve including at least one opened end and being formed from elastic material to receive, when in an expanded condition, the internal body tissue to be constricted and to constrict the internal body tissue when released from the expanded condition; and
    a tear resistance structure about the sleeve that precludes propagation of a tear in the sleeve.

2. The device of claim 1 wherein the tear resistance structure is an increased thickness of the sleeve.

3. The device of claim 1 wherein the tear resistance structure is a plurality of ribs in the sleeve.

4. The device of claim 3 wherein the plurality of ribs include a first plurality of ribs and a second plurality of ribs and wherein the first and second pluralities of ribs intersect each other.

5. The device of claim 4 wherein the first and second pluralities of ribs intersect each other to form a pattern of squares.

6. The device of claim 4 wherein the first and second pluralities of ribs intersect each other to form a pattern of diamonds.

7. The device of claim 4 wherein one of the first and second pluralities of ribs forms a pattern of waves.

8. The device of claim 7 wherein the pattern of waves is circumferential about the sleeve.

9. The device of claim 3 wherein the plurality of ribs forms a knurl pattern.

10. The device of claim 1 wherein the tear resistance structure is on an inner surface of the sleeve.

11. A constriction device that constricts internal body tissue, the device comprising:
    implantable sleeve means formed of elastic material for constricting internal body tissue received therein; and
    tear resistance means about the sleeve means for precluding propagation of a tear in the sleeve means.

12. The device of claim 11 wherein the tear resistance means is an increased thickness of the sleeve.

13. The device of claim 11 wherein the tear resistance means is a plurality of ribs in the sleeve.

14. The device of claim 13 wherein the plurality of ribs include a first plurality of ribs and a second plurality of ribs and wherein the first and second pluralities of ribs intersect each other.

15. The device of claim 14 wherein the first and second pluralities of ribs intersect each other to form a pattern of squares.

16. The device of claim 14 wherein the first and second pluralities of ribs intersect each other to form a pattern of diamonds.

17. The device of claim 14 wherein one of the first and second pluralities of ribs forms a pattern of waves.

18. The device of claim 17 wherein the pattern of waves is circumferential about the sleeve.

19. The device of claim 13 wherein the plurality of ribs forms a knurl pattern.

20. The device of claim 11 wherein the tear resistance means is on an inner surface of the sleeve.

21. A constriction device that constricts internal body tissue, the device comprising:
    an implantable elongated sleeve including at least one opened end and being formed from elastic material to receive, when in an expanded condition, the internal body tissue to be constricted and to constrict the internal body tissue when released from the expanded condition,
    the elastic material of the elongated sleeve including a tear resistance structure that precludes propagation of a tear in the sleeve.

22. A constriction device that constricts internal body tissue, the device comprising:
    implantable sleeve means formed of elastic material for constricting internal body tissue received therein,
    the elastic material of the sleeve means including a tear resistance means for precluding propagation of a tear in the sleeve means.

23. A constriction device that constricts internal body tissue, the device comprising:
    implantable sleeve means for elastically constricting internal body tissue received therein, the sleeve means including a tear resistance means for precluding propagation of a tear in the sleeve means.

* * * * *